United States Patent
Majeed et al.

(10) Patent No.: US 12,240,808 B2
(45) Date of Patent: Mar. 4, 2025

(54) PROCESS FOR THE SYNTHESIS OF CALEBIN-A AND ITS INTERMEDIATES

(71) Applicants: Muhammed Majeed, Bangalore (IN); Kalyanam Nagabhushanam, East Windsor, NJ (US); Nagarajan Muthukaman, Bangalore (IN); Pentakota Paradesi Naidu, Bangalore (IN)

(72) Inventors: Muhammed Majeed, Bangalore (IN); Kalyanam Nagabhushanam, East Windsor, NJ (US); Nagarajan Muthukaman, Bangalore (IN); Pentakota Paradesi Naidu, Bangalore (IN)

(*) Notice: Subject to any disclaimer, the term of this patent is extended or adjusted under 35 U.S.C. 154(b) by 217 days.

(21) Appl. No.: 17/825,689

(22) Filed: May 26, 2022

(65) Prior Publication Data
US 2022/0388939 A1   Dec. 8, 2022

Related U.S. Application Data

(60) Provisional application No. 63/194,465, filed on May 28, 2021.

(51) Int. Cl.
| | |
|---|---|
| *C07C 67/08* | (2006.01) |
| *C07C 67/11* | (2006.01) |
| *C07C 67/293* | (2006.01) |
| *C07C 69/734* | (2006.01) |
| *C07C 69/736* | (2006.01) |

(52) U.S. Cl.
CPC .............. *C07C 67/08* (2013.01); *C07C 67/11* (2013.01); *C07C 67/293* (2013.01); *C07C 69/734* (2013.01); *C07C 69/736* (2013.01); *C07C 2601/16* (2017.05)

(58) Field of Classification Search
None
See application file for complete search history.

(56) References Cited

U.S. PATENT DOCUMENTS

| | | | |
|---|---|---|---|
| 2016/0002141 A1* | 1/2016 | Majeed | C07C 67/10 560/75 |
| 2022/0204462 A1* | 6/2022 | Kayed | C07C 49/255 |

OTHER PUBLICATIONS

National Center for Biotechnology Information. PubChem Compound Summary for CID 78280877 (CID '877), 2-Oxopropyl 3-(4-hydroxy-3-methoxyphenyl)prop-2-enoate. https://pubchem.ncbi.nlm.nih.gov/compound/78280877. Accessed Feb. 22, 2024, first published in PubChem on Oct. 6, 2014 (Year: 2014).*
Fache ("Total synthesis of cimiracemate B and analogs" Tetrahedron, 2005, p. 5261) (Year: 2005).*
Kim ("Total synthesis of Calebin-A, Preparation of Its Analogues, and Their Neuronal Cell Protectivity Against b-Amyloid Insult" Bioorg. Med. Chem. Lett. 2001, p. 2541) (Year: 2001).*

* cited by examiner

*Primary Examiner* — Amy C Bonaparte

(57) ABSTRACT

The invention discloses novel intermediates in the synthesis of Calebin A represented by formula 3. The invention also covers processes for the synthesis of Calebin-A and its analogs using compounds of formula 3.

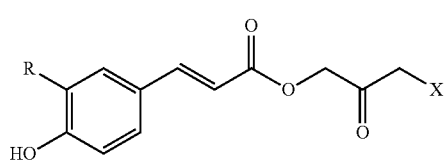

6 Claims, No Drawings

PROCESS FOR THE SYNTHESIS OF CALEBIN-A AND ITS INTERMEDIATES

CROSS REFERENCE TO RELATED APPLICATIONS

This application is a non-provisional filing claiming priority from U.S. provisional application No. 63/194,465 filed on 28 May 2021, the contents of which are incorporated herein by reference.

FIELD OF INVENTION

The present invention in general relates to Calebin-A. More specifically, the present invention relates to a novel process for the preparation of Calebin-A, and its analogs

DESCRIPTION OF PRIOR ART

Calebin-A, also known as Feruloylmethyl ferulate, is a novel curcuminoid related structure obtained from rhizomes of *Curcuma longa*, Zingiberaceae. Calebin-A is naturally present in the rhizomes of *Curcuma longa* in trace amounts. It was first isolated and identified by Darrick S. H. L. Kim and So-Young Park (J. Nat. Prod., 2002, 65, 1227-1231) from *Curcuma longa* in 2001. Its analogs were synthesized by Kim, D. S. H. L. & Kim, J. Y. in 2001 (Bioorg. Med. Chem. Lett., 2001, 11, 2541-2543). Calebin-A has been reported to elicit various biological functions, some of which are mentioned in the following prior art documents:

1. Calebin A, a novel component of turmeric, suppresses NF-rJB regulated cell survival and inflammatory gene products leading to inhibition of cell growth and chemosensitization, Tyagi et. al., Phytomedicine. 2017 Oct. 15; 34: 171-181.
2. Calebin-A induces cell cycle arrest in human colon cancer cells and xenografts in nude mice, Liou et. al., Journal of Functional Foods, Volume 26, October 2016, Pages 781-791
3. Majeed et al., Anti-obesity potential of Calebin A, U.S. Pat. No. 9,328,330.
4. Majeed et. al., Method for the treatment of hypercholesterolemia, U.S. Pat. No. 9,668,999.
5. Majeed et. al., Calebin A for hepatic steatosis, U.S. Pat. No. 9,737,502.
6. Majeed et. al., Composition and method for the protection of articular cartilage, U.S. Pat. No. 9,220,703.
7. Majeed et. al., Calebin A for osteoporosis, U.S. Pat. No. 9,539,232

There are many commercial processes available for the preparation of Calebin-A and its pharmaceutically acceptable salts. Calebin-A and its derivatives were isolated and synthesised by Yong et. al., (Chem. Pharm. Bull. 55(6) 940-943 (2007)) and Majeed et. al., (Georg Thieme Verlag Stuttgart • New York—SynOpen 2017, 1, 125-128). Majeed et. al. also disclosed a process for the synthesis of Calebin-A and its biologically active analogs (U.S. Pat. No. 9,365,486).

However, the above processes either involves multi-steps or commercially not viable. Hence there is need to develop a commercially viable, safe, simple and scalable process for the large scale production of Calebin-A and its analogs.

The present invention fulfils the aforesaid objectives by disclosing a simple, scalable, industrially advantageous and cost-effective process for the synthesis of Calebin-A.

SUMMARY OF THE INVENTION

The present invention discloses novel synthetic schemes for the preparation of Calebin-A. More specifically, the invention discloses simple, scalable, industrially advantageous and cost-effective process for the synthesis of Calebin-A, its analogs.

Another advantage is that the current process circumvents the use of expensive, hazardous reagents, and solvents. Further, the current synthetic process involves two step syntheses from ferulic acid (commercially available) which is a green process, environmentally friendly and industrially scalable.

The present invention also discloses a process for the synthesis of Calebin-A through new previously not disclosed intermediates starting from substituted cinnamic acids and substituted aromatic aldehydes.

Other features and advantages of the present invention will become apparent from the following more detailed description,

DETAILED DESCRIPTION OF THE MOST PREFERRED EMBODIMENT

In the most preferred embodiment of the invention includes a compound of general formula 3 represented below

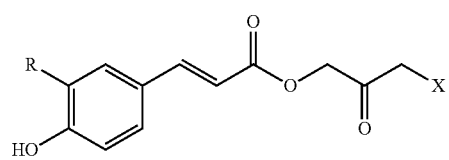

wherein X is selected from the group consisting of Cl, Br, I, and H; and R is selected from the group consisting of OMe, and H.

In another most preferred embodiment of the invention relates to a process for the preparation of Calebin-A and its analogs represented by general formula 5 from general formula 3 (Example 4),

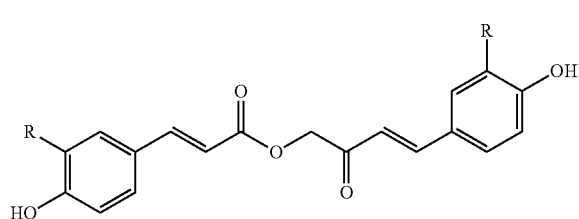

comprising:
a) Reacting compound of formula 1 with compound of formula 2 in presence of a solvent and sodium bicarbonate (Examples 1-3) or in presence of potassium iodide, potassium carbonate, and 1,2 dibromoethane to obtain compounds of general formula 3 (Example 5)

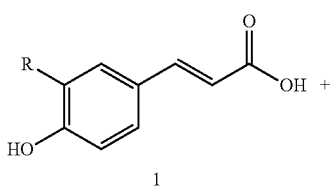

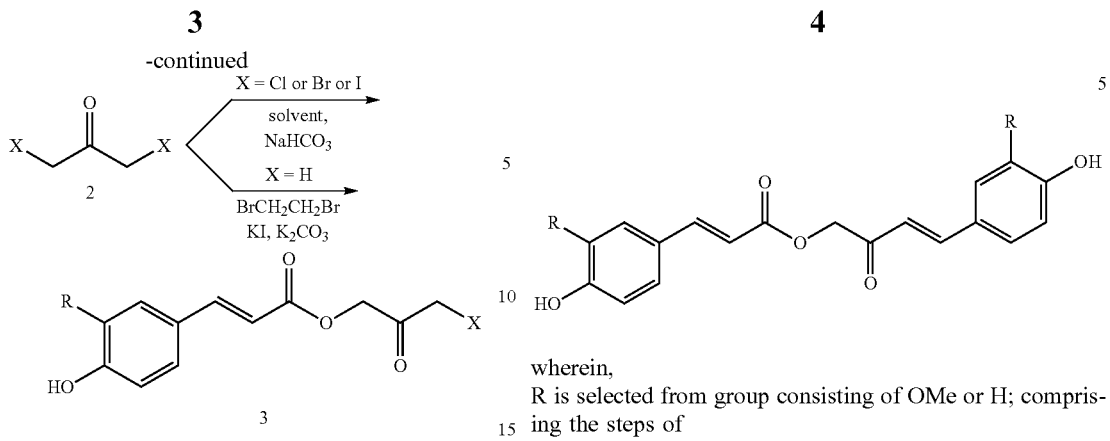

b) Reacting compound of formula 3 with triphenyl phosphine (TPP), in presence of sodium carbonate and a solvent followed by compound of formula 4 (Example 4) or reacting compound of formula 3 with compound of formula 4, in presence of an organo catalyst and methanol to obtain compound represented by formula 5 (Example 6):

wherein, R is selected from group consisting of OMe or H; and X is selected from the group consisting of Cl, Br, I, and H In a related embodiment of the invention, the solvent from step a) is selected from the group consisting of N, N-dimethyl formamide, dimethyl sulfoxide, N-methyl-2-pyrrolidone, acetone, acetonitrile, tetrahydrofuran and dioxane.

In related embodiment of the invention, the solvent from step b) is selected from the group consisting of acetonitrile, tetrahydrofuran, 1,4 dioxane, diisopropyl methyl ether, dimethoxy ethane, cyclopentyl methyl ether, 2-methyl tetrahydrofuran, methyl tert-butyl ether, methanol, and ethanol.

In related embodiment of the invention, the organo catalyst is selected from the group consisting of L-proline, 4-hydroxy L-proline, L-piperidine-2-carboxylic acid, L-azetidine-2-carboxylic acid, S-(−)-indoline-2-carboxylic acid or L-4-thiazolidinecarboxylic acid. The product obtained from using this process is not chiral, the optical antipodes of the preceding amino acids, namely the D-series of amino acids is obvious for the skilled person to use in the place of L-amino acids.

In yet another most preferred embodiment invention relates to a process for the preparation of Calebin-A and its analogs represented by formula 5 (Example 7), wherein,
R is selected from group consisting of OMe or H; comprising the steps of
a) mixing hydroxy acetone represented by formula 6 with pyridine in a reaction flask containing dichloromethane and cooling the reaction mixture of step to 0-5° C.;
b) adding acetyl chloride to the reaction mixture slowly at a temperature of 0-5° C. initially and further stirred at room temperature for 5 hours;
c) diluting the reaction mass with water and washing with brine;
d) separating the organic layer to obtain compound of formula 7,
e) charging compound of formula 7 from step d) into a reaction flask containing ethanol:water mixture (1:1) along with calcium hydroxide, and compound of formula 4;
f) heating the reaction mixture to 50° C. for 15 h and cooling the reaction mass after completion of reaction followed by filtering the resultant solid;
g) washing the resultant solid of step f) with ethanol:water mixture, concentrating the reaction mixture and drying under vacuum to yield Calebin A or its analogs as represented by general formula 5, -continued

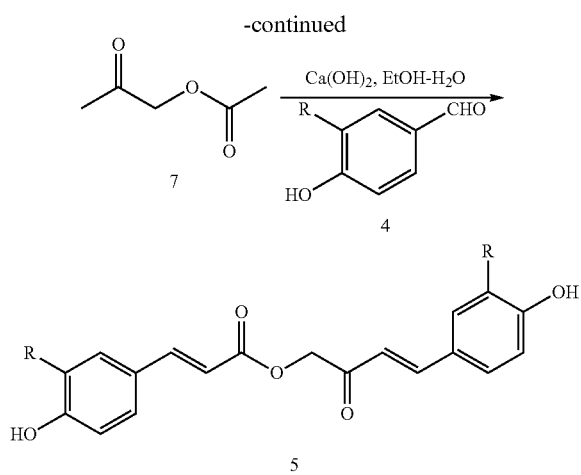

wherein, R is selected from group consisting of OMe or H.

EXAMPLES

Example-1: Preparation of feruloyl chloro acetonyl ester (3, X=Cl)

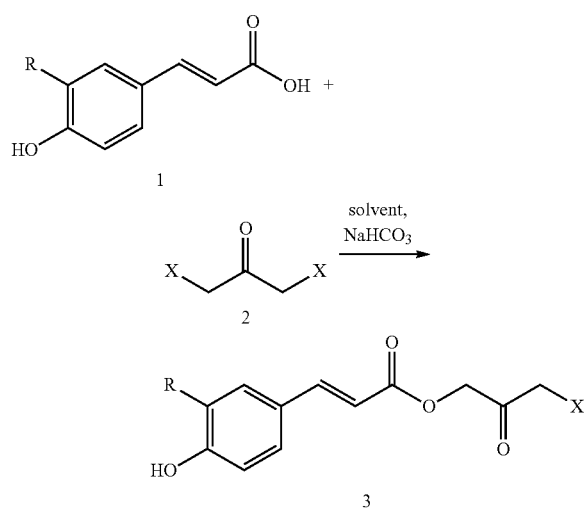

To a solution of compound of formula 1 (5 g, 0.0257 mol) in N, N-dimethyl formamide (15.0 mL), charged 1,3-dichloroacetone (6.54 g, 0.0515 mol), sodium bicarbonate (2.4 g, 0.0515 mol) and stirred for 30 min at room temperature. The reaction mass was then heated to 50-55° C., maintained for 15 h and cooled to room temperature. After the completion of reaction, water (15 ml) and ethyl acetate (25 ml) were added to the above reaction mass. The separated organic layer was washed with sodium bicarbonate (20 ml) and brine solution. The ethyl acetate layer was distilled-off and diluted with toluene to afford solid. The resultant solid was filtered and dried at 65-70° C. for 15 h under reduced pressure to yield feruloyl chloro acetonyl ester 3 as brown colour solid. Mp=123.1-126.5° C.;

$^1$H NMR (300 MHz, Dimethyl sulfoxide-$d_6$): δ 3.80 (s, 3H), 4.60 (s, 2H), 4.98 (s, 2H), 6.57-6.52 (d, J=15.9 Hz, 1H), 6.80-6.77 (d, J=8.4 Hz, 1H), 7.714-7.12 (d, J=7.5 Hz, 1H), 7.34 (s, 1H), 7.62-7.57 (d, J=15.9 Hz, 1H);

$^{13}$C NMR (100 MHz. Dimethyl sulfoxide-$d_6$): 46.91, 56.13, 66.63, 111.73, 113.75, 115.95, 123.92, 125.86, 146.70, 148.37, 150.05, 166.29, 197.00.

Example-2: Preparation of feruloyl bromo acetonyl ester (3, X=Br)

To a solution of compound of formula 1 (5 g, 0.0257 mol) in N, N-dimethyl formamide (15.0 mL), charged 1,3-dibromoacetone (11.0 g, 0.0515 mol) and sodium bicarbonate (2.4 g, 0.0283 mol) stirred for 30 min at room temperature. The reaction mass was then heated to 50-55° C., maintained for 15 h and cooled to room temperature. After the completion of reaction, water (15 ml) and ethyl acetate (25 ml) were added to the above reaction mass. The separated organic layer was washed with sodium bicarbonate (20 ml) and brine solution. The ethyl acetate layer was distilled-off and diluted with toluene to afford solid. The resultant solid was filtered and dried at 65-70° C. for 15 h under reduced pressure to yield feruloyl bromo acetonyl ester.

1H NMR (300 MHz, Dimethyl sulfoxide-$d_6$): δ 3.73 (s, 3H), 4.56 (s, 2H), 5.21 (s, 2H), 6.57-6.52 (d, J=15.8 Hz, 1H), 6.79-6.76 (d, J=9 Hz 1H), 7.13-7.10 (d, J=9 Hz, 1H), 7.34 (s, 1H), 7.62-7.57 (d, J=15.9 Hz, 1H);

Example-3: Preparation of feruloyl iodo acetonyl ester (3, X=I)

To a solution of compound of formula 1 (5 g, 0.0257 mol) in N, N-dimethyl formamide (15.0 mL), charged 1,3-diiodoacetone (15.9 g, 0.0515 mol) and sodium bicarbonate (2.4 g, 0.0283 mol) stirred for 30 min at room temperature. The reaction mass was then heated to 50-55° C., maintained for 15 h and cooled to room temperature. After the completion of reaction, water (15 ml) and ethyl acetate (25 ml) were added to the above reaction mass. The separated organic layer was washed with sodium bicarbonate (20 ml) and brine solution. The ethyl acetate layer was distilled-off and diluted with toluene to afford solid. The resultant solid was filtered and dried at 65-70° C. for 15 h under reduced pressure to yield feruloyl iodo acetonyl ester.

1H NMR (300 MHz, Dimethyl sulfoxide-$d_6$): δ 3.80 (s, 3H), 4.60 (s, 2H), 4.82 (s, 2H), 6.55-6.50 (d, J=15 Hz, 1H), 6.79-6.76 (d, J=9 Hz 1H), 7.13-7.10 (d, J=9 Hz, 1H), 7.32 (s, 1H), 7.59-7.54 (d, J=15 Hz, 1H);

13C NMR (100 MHz, Dimethyl sulfoxide-$d_6$): 46.91, 56.09, 68.55, 111.63, 114.04, 115.93, 123.78, 125.88, 146.34, 148.35, 149.94, 166.37, 202.58.

(For the preparation of 1,3-diiodoacetone, Exact reference is: Femanda Priscila N. R. da Silva et al, J. Braz. Chem. Soc., 2020, 31(8), 1725-1731.

Example-4: Preparation of Calebin-A [3-(4-Hydroxy-3-methoxy-phenyl)-acrylic acid 4-(4-hydroxy-3-methoxy-phenyl)-2-oxo-but-3-enyl ester] (5)

Triphenylphosphine (5.04 g, 0.0192 mol) was charged into the reaction flask containing compound of formula 3 (when X=Cl or Br or I) (5 g, 0.0175 mol) in methanol (30 ml) and the reaction mixture was then heated to 60-65° C. for 20 h. After the reaction completion, reaction mass was cooled to room temperature and charged 15 ml of 10% sodium carbonate solution for 1 h and further stirred at that temperature for 12 h. The resultant solid was cooled to 0-5° C. for 3 h. The solid was filtered-off and further washed with chilled methanol (5 mL). The above wet cake was taken into RB flask and added cyclopentyl methyl ether (40 mL), followed by compound of formula 4 (2.92 g, 0.0192 mol) and further heated the reaction mass to 80-85° C. and maintained for 15 h. The reaction mass was cooled to 25-35° C. and maintain at that temperature for 15 h. The observed solid was cooled to 0-5° C. for 3 h. The resultant solid was filtered and washed with chilled methanol (10 mL). The compound was dried under high vacuum at 85-90° C. for 15 h to yield Calebin-A (5) as off white to buff colour. MP=146-154° C.;

$^1$H NMR (300 MHz, Dimethyl sulfoxide-$d_6$) δ 3.79 (s, 6H), 5.13 (s, 2H), 6.61-6.56 (d, J=15.9 Hz, 1H), 6.86-6.81 (m, 3H), 7.17-7.13 (t, 2H), 7.35-7.33 (d, J=6.9 Hz, 2H), 7.64-7.59 (d, J=15.9 Hz, 2H), 9.69 (bs, 2H);

$^{13}$C NMR (100 MHz. Dimethyl sulfoxide-$d_6$): 56.08, 56.13, 67.55, 111.71, 111.74, 114.27, 115.95, 116.07, 119.87, 123.77, 124.14, 125.96, 126.06, 144.24, 146.24, 148.37, 148.40, 149.93, 150.23, 166.50, 193.01.

Example-5: Preparation of 3-(4-hydroxy-3-methoxy-phenyl)-acrylic acid-2-oxo-propyl ester (3, X=H)

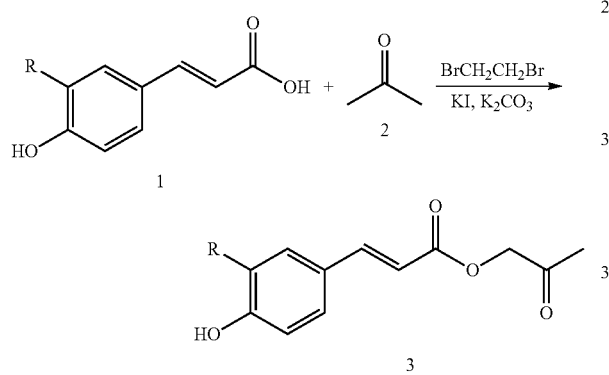

The process was performed based on reported procedure (Augustine et. al., Tetrahedron Letters Volume 55, Issue 24, 11 Jun. 2014, Pages 3503-3506; Wang et. al., Chinese Chemical Letters, Volume 31, Issue 3, March 2020, Pages 711-714). Compound of formula 1 (5 g, 0.0257 mol), potassium carbonate (5.3 g, 0.0385 mol), potassium iodide (0.6 g, 0.0035 mol), and 1,2-dibromo ethane (3.5 ml, 0.0403 mol) were charged into the reaction flask containing acetone (25 ml) and the reaction mixture was further heated to 50-55° C. After the reaction completion, the reaction mass was filtered, and the inorganic salts were separated. The filtrate was distilled-off and further diluted with water, and toluene and stirred for 1 h. The organic portion was separated and concentrated to afford compound 3 as semi-solid.

$^1$H NMR (300 MHz, Dimethyl sulfoxide-$d_6$) δ 2.28 (s, 3H), 4.0 (s, 3H), 4.78 (s, 2H), 5.95 (s, 1H), 6.40-6.36 (d, J=6.9 Hz, 1H), 6.94-6.92 (d, J=5.1 Hz, 1H), 7.08-7.70 (m, 2H), 7.73-7.67 (d, J=16.5 Hz, 1H).

Example-6: Preparation of Calebin-A, 3-(4-Hydroxy-3-methoxy-phenyl)-acrylic acid 4-(4-hydroxy-3-methoxy-phenyl)-2-oxo-but-3-enyl ester (5)

Compound 3 (5 g, 0.02 mol), L-Proline (2.3 g, 0.02 mol), compound of formula 4 (3.3 g, 0.02 mol), were charged into the reaction flask containing methanol (25 ml) and the reaction mixture was further heated to 60-65° C. for 10 h.

The reaction mass was cooled, and the resultant solid was filtered-off. The obtained solid was further washed with methanol (2×50 mL) to afford Calebin-A, 4 as an off-white to buff colour solid. Mp=151° C. For analytical data, refer Example-4.

Example-7: Preparation of Acetic acid 2-oxo-propyl ester (7)

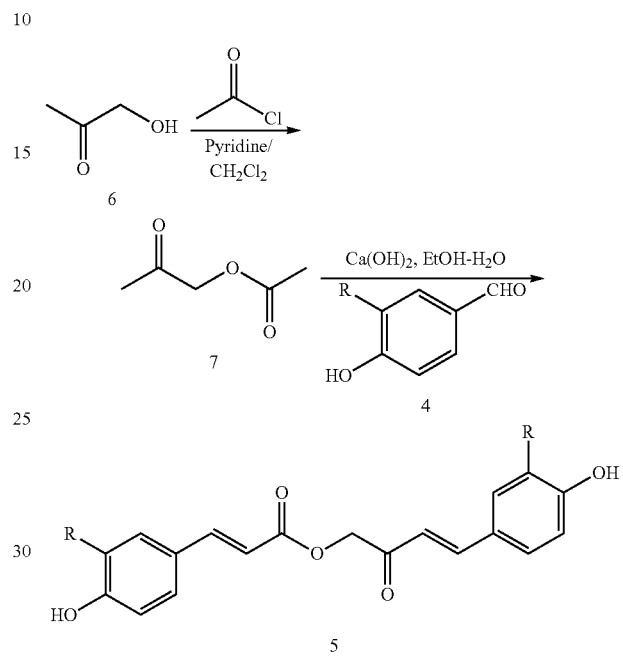

The compound was first referred by Yang, Yu et al, From *Journal of Fluorine Chemistry*, 2006, 127(2), 277-281) and the process is based on the reference Lei Yu et. al. Scientific Reports, 2016, 6, 30432). Hydroxyacetone 6 (5 g, 0.0675 mol) and pyridine (5.3 ml, 0.0675 mol) were charged into the reaction flask containing dichloromethane (30 ml), and the reaction mixture was further cooled to 0-5° C. Next, acetyl chloride (5.3 ml, 0.0743 mol) was added slowly to the reaction mixture at that temperature and further stirred at room temperature for 5 h. After the reaction completion, the reaction mass was diluted with water, washed with brine. The organic layer was separated and concentrated to afford Compound 7 (acetic acid 2-oxo-propyl ester) as semi solid.

$^1$H NMR (300 MHz, Dimethyl sulfoxide-$d_6$): δ 4.66 (s, 2H), 2.17 (s, 6H).

$^{13}$C NMR (100 MHz, Dimethyl sulfoxide-$d_6$): 201.5, 170.2, 68.3

Example-8: Preparation of Calebin-A, 3-(4-Hydroxy-3-methoxy-phenyl)-acrylic acid 4-(4-hydroxy-3-methoxy-phenyl)-2-oxo-but-3-enyl ester (5)

Acetic acid 2-oxo-propyl ester 7 (5 g, 0.043 mol), calcium hydroxide (6.3 ml, 0.086 mol), compound of formula 4 (7.2 g, 0.047 mol), were charged into the reaction flask containing ethanol-water mixture (30 ml, 1:1) and the reaction mixture was further heated to 50° C. for 15 h. After the reaction completion, cool the reaction mass and the resultant solid was filtered-off. The solid was further washed with ethanol-water mixture (2×50 mL), dried under vacuum to afford Calebin-A, 5 as an off-white solid. For analytical data, refer Example-4.

While the invention has been described with reference to a preferred embodiment, it is to be clearly understood by those skilled in the art that the invention is not limited thereto, and salts of sodium or potassium is also obvious for skilled artisan, which can also be prepared by this process. The scope of the invention is to be interpreted in conjunction with the appended claims.

We claim:
1. A compound of general formula 3 represented below

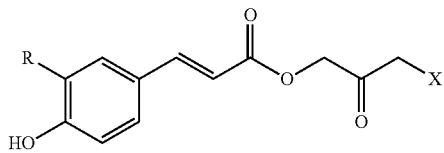

wherein X is selected from the group consisting of Cl, Br, and I; and
R is selected from the group consisting of OMe, and H.

2. A process for the preparation of Calebin-A, and its analogs represented by general formula 5, from general formula 3,

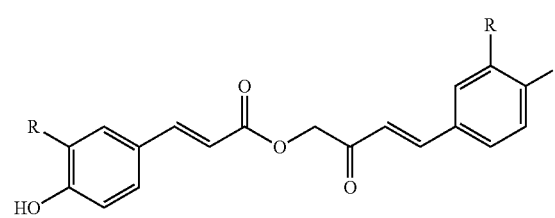

comprising:
a) reacting a compound of formula 1 with a compound of formula 2 in the presence of a solvent and sodium bicarbonate or in the presence of potassium iodide, potassium carbonate, and 1,2 dibromoethane to obtain a compound of formula 3

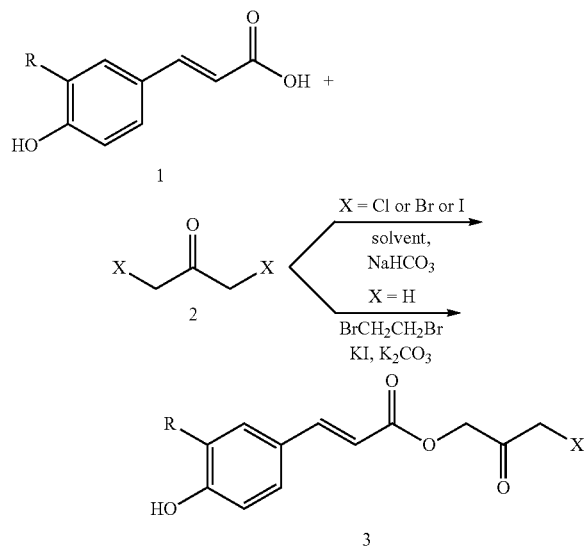

b) reacting a compound of formula 3 with triphenyl phosphine (TPP), in the presence of a solvent under reflux, cooling, and then charging with sodium carbonate followed by a compound of formula 4 or reacting a compound of formula 3 with a compound of formula 4, in the presence of an organo catalyst and methanol to obtain a compound represented by formula 5:

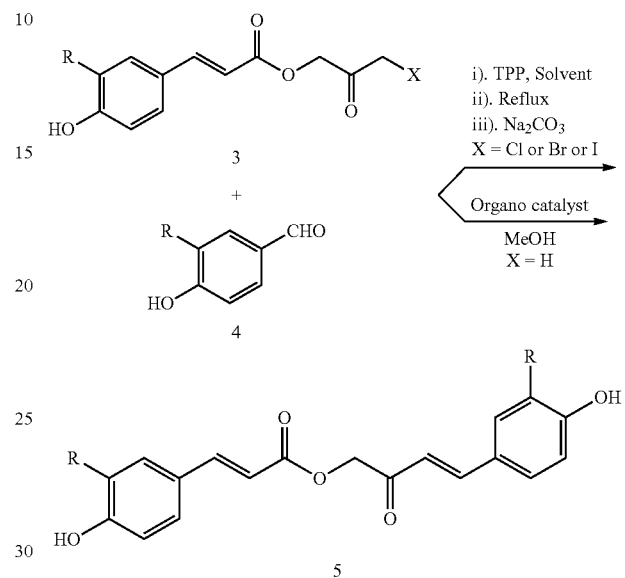

wherein, R is selected from the group consisting of OMe and H; and X is selected from the group consisting of Cl, Br, I, and H.

3. The process as in claim 2, wherein the solvent from step a) is selected from the group consisting of N, N-dimethyl formamide, dimethyl sulfoxide, N-methyl-2-pyrrolidone, acetone, acetonitrile, tetrahydrofuran and dioxane.

4. The process as in claim 2, wherein the solvent from step b) is selected from the group consisting of acetonitrile, tetrahydrofuran, 1,4-dioxane, diisopropyl methyl ether, dimethoxy ethane, cyclopentyl methyl ether, 2-methyl tetrahydrofuran, methyl tert-butyl ether, methanol, and ethanol.

5. The process as in claim 2, wherein the organo catalyst is selected from the group consisting of L-proline, 4-hydroxy L-proline, L-piperidine-2-carboxylic acid, L-azetidine-2-carboxylic acid, S-(−)-indoline-2-carboxylic acid, and L-4-thiazolidinecarboxylic acid.

6. A process for the preparation of Calebin-A, and its analogs represented by general formula 5,

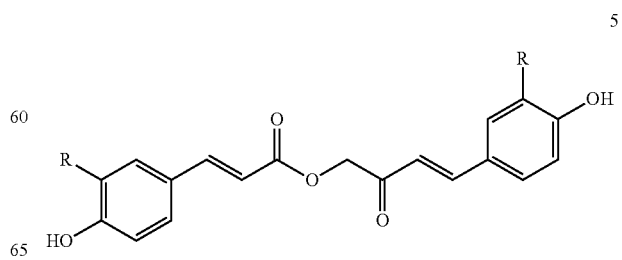

wherein,

R is selected from group consisting of OMe and H;

comprising the steps of a) mixing hydroxy acetone represented by formula 6 with pyridine in a reaction flask containing dichloromethane and cooling to 0-5° C.;
b) adding acetyl chloride to the reaction mixture slowly at a temperature of 0-5° C. and then stirring at room temperature for 5 hours;
c) diluting the reaction mass with water and washing with brine;
d) separating the organic layer to obtain a compound of formula 7,
e) charging compound of formula 7 from step d) into a reaction flask containing a 1:1 (v/v) ethanol:water mixture, calcium hydroxide, and a compound of formula 4;
f) heating the reaction mixture to 50° C. for 15 h and cooling the reaction mass after completion of reaction to produce a solid, followed by filtering the resultant solid;
g) washing the resultant solid of step f) with an ethanol: water mixture, concentrating the reaction mixture and drying under vacuum to yield Calebin A or its analogs as represented by general formula 5.

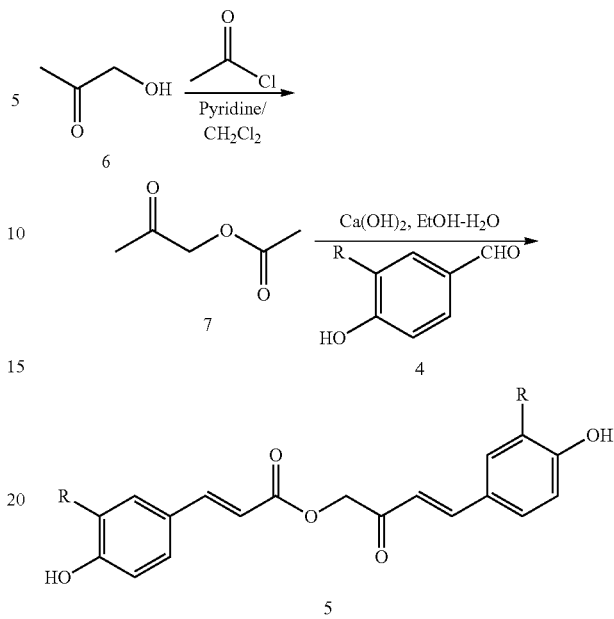

* * * * *